United States Patent [19]

Thon

[11] Patent Number: 4,949,706
[45] Date of Patent: Aug. 21, 1990

[54] SIDE-VIEWING ENDOSCOPE

[76] Inventor: Hans J. Thon, Lindenweg 26, D-5305 Alfter-Oedekoven, Fed. Rep. of Germany

[21] Appl. No.: 159,965

[22] PCT Filed: Jun. 25, 1987

[86] PCT No.: PCT/DE87/00287
 § 371 Date: Apr. 21, 1988
 § 102(e) Date: Apr. 21, 1988

[87] PCT Pub. No.: WO88/00020
 PCT Pub. Date: Jan. 14, 1988

[30] Foreign Application Priority Data

Jun. 27, 1986 [DE] Fed. Rep. of Germany ....... 3621509

[51] Int. Cl.$^5$ .............................................. A61B 1/00
[52] U.S. Cl. ...................................................... 128/4
[58] Field of Search ................................ 128/4, 5, 6, 7

[56] References Cited

U.S. PATENT DOCUMENTS 1,901,731 3/1933 Buerger .................................. 128/7

FOREIGN PATENT DOCUMENTS 480520 8/1929 Fed. Rep. of Germany .
2653661 4/1982 Fed. Rep. of Germany .
 711.949 9/1931 France .

*Primary Examiner*—William H. Grieb
*Attorney, Agent, or Firm*—Hill, Van Santen, Steadman & Simpson

[57] ABSTRACT

A side-viewing endoscope comprises an instrumentation channel (8) that forms an outlet opening in the operative region (distal end) and comprises a deflecting element (14) as well as an actuation means for the latter.

In order to guarantee an axially suited power transmission in an optimum operative region, it is provided that the instrumentation channel (8) comprises a curved section (10) at the exit end and that the instrumentation channel (8) is directed toward the lateral wall of the endoscope in the operative region.

15 Claims, 2 Drawing Sheets

SIDE-VIEWING ENDOSCOPE

The invention is directed to a side-viewing endoscope comprising an instrumentation channel that forms an outlet opening in the operative region (distal end), and comprising a deflection element as well as an actuation means for the latter.

Side-viewing endoscopes serve for endoscopic examination of, in particular, the duodenum of life forms, particularly for the portrayal of the papilla vateri (duct opening of the gall and pancreatic issue), with the possibility of introducing instruments (catheters, brushes, tissue forceps, slings) into the pancreatic duct as well as into the biliferous duct in order to thus be able to carry out diagnostic or, respectively, therapeutic measures for the implantation of endoprotheses as well.

In side-viewing endoscopes previously available as known, for example, from the brochure Duodenoscope DUO-X, DUO-XL 181-3-3 of Fujinon Optical Incorporated, the operative region of the endoscope is of such a nature that the instrumentation channel guided in the endoscope shaft and exits in the direction of the longitudinal axis of the endoscope in a small shaft at the distal end. The exit angle of the complement of instruments guided through the instrumentation channel can be varied by a deflecting element that is attached in this shaft, and this deflecting element is capable of being mechanically moved from the head end of the endoscope. Given a completely relaxed deflecting element, the complement of instruments (catheter, guide wire, permanent catheter) distally emerges at an angle of about 30°-40° relative to the longitudinal axis of the endoscope. Given complete angling of the deflecting element, an exit angle of a maximum of 90° relative to the longitudinal axis of the endoscope can be achieved.

As a consequence of structurally conditioned circumstances, a guidance of the complement of instruments in the sense of an elastic line does not arise given complete angling; on the contrary, the formation of a buckling at the level of the outlet location of the instrumentation channel occurs in the operating shaft. As a result thereof, great frictional forces arise both due to the buckling at the outlet opening of the instrumentation channel as well as at the inside surface of the angling lever. Dependent on the caliber of the complement of instruments and the inherent stiffness thereof, a further advance is then made considerably more difficult or, respectively, impossible. Particularly given the employment of stiff instrumentations such as large-caliber permanent catheters, shearing forces or, respectively, tangential forces that do not allow any axially suited power transmission and, thus, that do not represent an optimal solution for the introduction of, in particular, stiff instrumentations arise upon deflection with the deflecting element, arising as a consequence of the stiffness of the material.

SUMMARY OF THE INVENTION

It is therefore the object of the invention to improve a side-viewing endoscope of the species initially cited such that an axially suited power transmission is possible and, thus, an optimum solution for the introduction of, in particular, stiff, large-caliber instrumentations is created.

This object is inventively achieved in that the instrumentation channel comprises a prescribed curvature at the outlet end and, in the operative region, is directed toward the outlet opening provided in the lateral wall of the endoscope.

The inventive solution creates a side-viewing endoscope that avoids the appearance of shearing or, respectively, tangential forces even given large-caliber and stiff complements of instruments such as, for example, large-caliber permanet catheters, so that an axially suited power transmission is possible. Since shearing forces are eliminated to the farthest-reaching degree, dislocations of the complement of instruments in a distal direction that lead to an interruption of the introduction in the known devices practically no longer occur. Given a correct position of the distal end in the middle of the descending branch of the duodenum, the invention particularly enables the introduction of complements of instruments (such as, for example, guide wire or permanent catheter), into the biliferous duct in a relatively simple way, with a deflection in the range of about 90°-120° relative to the longitudinal axis of the endoscope being required for this purpose.

An advantageous embodiment of the invention provides that the deflecting element is seated in the region of the curvature and can be moved with the actuation means into a position in which, being adjacent to the curved region, it laterally projects out of the endoscope. Given correct position of the distal end of the side-viewing endoscope in the middle of the descending branch of the duodenum, a deflection of the complement of instruments having an angle between 90° and 120° relative to the longitudinal axis of the endoscope must be achieved in order for the complement of instruments (for example, guide wire or permanent catheter) to penetrate into the biliferous duct in order to achieve an axially suited thrust transmission that corresponds to the position of the biliferous duct. This condition is established in this preferred embodiment since deflection in the range between 70° and at least 120° is enabled here.

It is provided in a further, advantageous embodiment of the invention that the actuation means comprises mechanical means that lead from a head part of the endoscope to the deflecting element. The deflecting element can be extended and retracted in a simple way with the assistance of this mechanical actuation means, whereby intermediate positions are also enabled.

In a very practical way, the deflecting element is executed curved, whereby the radius of curvature of the deflecting lever corresponds to the radius of curvature of the curved region of the instrumentation channel or, respectively, is matched to the latter. The deflecting element can exhibit different shapes in cross-section and, in particular, can be fashioned as a closed or, respectively, partially opened sleeve or, respectively, can be fashioned channel-like. A good guidance in the region of the deflecting element as well is achieved on the basis of this fashioning.

Another development of the invention provides that the instrumentation channel is conducted closed up to the lateral surface of the endoscope. The deflecting element then extends adjacent to the closed region, so that a good guidance of the complement of instruments is handled without transition.

The bearing for the deflecting element can be fashioned as a pivot bearing. Advantageously, however, this bearing is fashioned as a sliding bearing since less space is used for the extension motion given such a bearing.

In order to minimize frictional forces when extending the deflecting element, the deflecting element and/or the sliding bearing is expediently provided with a glide coat. An execution of the bearing as a rolling bearing also comes into consideration when the frictional forces upon actuation of the deflecting element are to be minimized. In the curved region of the instrumentation channel, the curvature and the diameter of the instrumentation channel are expediently matched such to one another that the complement of instruments guided through the instrumentation channel emerges from the lateral endoscope surface at an angle between 60° and 90° dependent upon lay.

In an extremely practical way, the deflecting element exhibits a curvature that, in particular, describes an angle of about 90°, so that the complement of instruments guided through the instrumentation channel is deflectable by about another 90° with the deflecting element.

In order to enable observation in the expanded operative region, an optical observation system is provided in another advantageous embodiment of the invention, this optical observation system comprising a light guide and a viewing bundle, whereby the system has an observation range of about 50° through 150°.

BRIEF DESCRIPTION OF THE DRAWINGS

An exemplary embodiment of the invention is shown in the drawing and shall be described below. Shown are.

DESCRIPTION OF THE PREFERRED EMBODIMENTS

Figure 1:
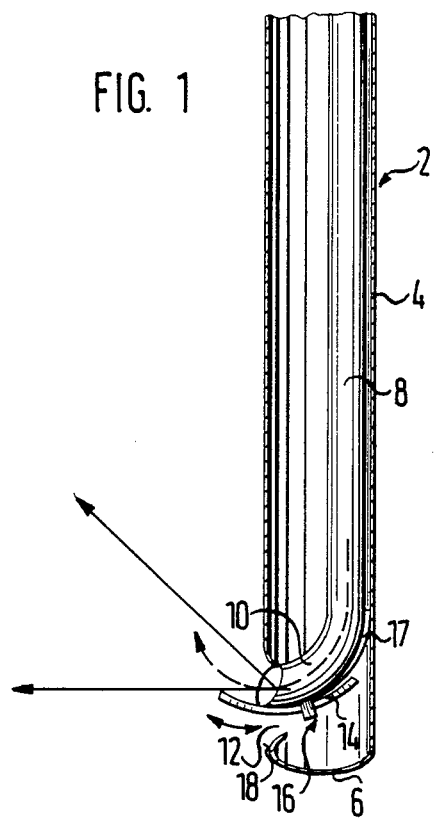
FIG. 1 is a longitudinal cross sectional view through the distal end of a sideviewing endoscope.
Figure 2:
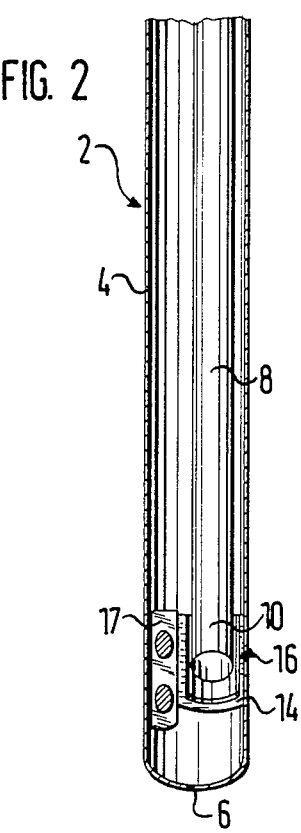
FIG. 2 is a longitudinal cross sectional view through the side-viewing endoscope shown in FIG. 1, being a section in a plane perpendicular to the plane of section according to FIG. 1.
Figure 3:
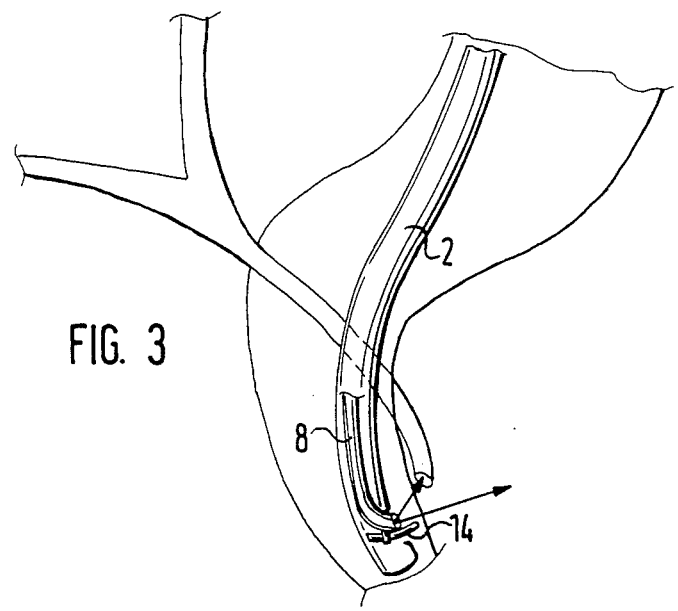
FIG. 3 is a schematic illustration of the side-viewing endoscope arranged in the descending branch of a duodenum, being shown in the region of the common outlet of biliferous duct and pancreatic duct.

FIGS. 1 and 2 shall be referenced first, these showing sectional views of the distal end, particularly of the operative region of a side-viewing endoscope 2. In this region, the sideviewing endoscope 2 is formed by a flexible, hose-like shaft part or, respectively, envelope member 4 that has a closure or, respectively, floor 6 at its end. An instrumentation channel 8 is arranged in the shaft part 4 whose other end is connected to a head part (not shown), this instrumentation channel 8 practically extending over the entire length of the shaft part 4, whereby the axes of the shaft part 4 and of the instrumentation channel 8 proceed essentially parallel to one another over the full length. The instrumentation channel 8 is thereby expediently laterally arranged in the proximity of the wall of the shaft part. The instrumentation channel 8 comprises a curved section 10 in the operative region. With prescribed curvature, the curved section 10 is guided closed up to the opposite side wall of the shaft part or, respectively, envelope member 4 and discharges toward the outside there. To this end, the shaft part 4 comprises an opening 12 in its wall. In order to avoid a dislocation of the curved section 10, the section is expediently secured to or, respectively, supported against the wall of the shaft part 4, as indicated at 17.

A deflecting element 14 is seated below the curved section 10. The bearing for the deflecting element 14 is fashioned as a sliding bearing 16 here. However, a pivot bearing can also be provided. In order to enable a displacement of the deflecting element 14, bearing jaws are laterally provided at the instrumentation channel 8., one of these bearing jaws being referenced 18. The deflecting element is displaceably seated between these bearing jaws 18. In order to be able to execute the displacement motion with the least possible exertion of force, the bearing jaws 18 can be provided with a ball bearing, with a roller bearing or with a needle bearing. Alternatively, a glide coat of the deflecting element and/or of the bearing jaws 18 also comes into consideration. A mechanical actuation means (not shown) by means of which the deflecting element can be actuated proceeding from the head part of the endoscope attacks at the back end of the deflecting element. The deflecting element 14 comprises a curvature both in longitudinal direction as well as in transverse direction. The curvature in longitudinal direction is thereby largely matched to the curvature of the instrumentation channel 8. Upon actuation with the actuation means (not shown), the deflecting element 14 is moved out of its quiescent position into an extended position. Since the bearing 16 is arranged in the region of the outlet of the instrumentation channel or, respectively, in the region of the opening 12, practically the entire deflecting element 14 extends outside of the envelope member in the extended position. In addition to the bending already achieved by the curvature of the instrumentation channel 8, a further bending region up to about 90° can be achieved with this dependent on the extent to which the deflecting element 14 is extended. Special measures in order to lend the deflecting element an adequately defined guidance in this position are required given a deflecting element extended by 90°. These additional measures, for example, can be comprised in a telescope-like design of the deflecting element.

The instrumentation channel is expediently composed of especially glidable and stable materials. Particularly coming into consideration here are ceramic or, respectively, plastic. The glide material can also be applied as a coating. The analogous case applies to the deflecting element 14.

The technical procedure upon introduction of a permanent catheter with the side-viewing endoscope of the invention shall be described below. First, the side-viewing endoscope has its distal end placed in the middle of the descending branch of the duodenum. A small papillotomy (slitting the outlet duct of the biliferous tract) is then carried out. After the subsequent introduction of a thin guide wire (Seldinger wire) into the biliferous duct, this being advanced into the intrahepatic biliferous tract under radiological observation, the permanent catheter is advanced into the instrumentation channel of the endoscope over the lying guide wire and, subsequently, is placed through the biliferous tract constriction with pressure with a feeding thrust catheter such that a derivation is guaranteed. Subsequently, the guide wire as well as the thrust catheter are removed through the instrumentation channel.

Figure 4:
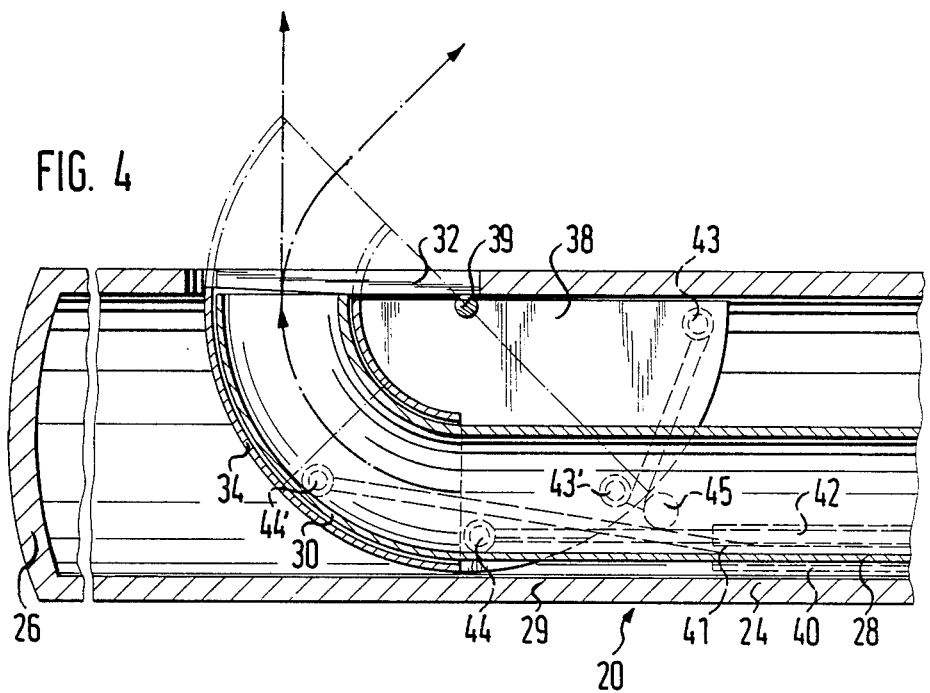
FIG. 4 is a cross sectional view through a practical execution of the distal end of a side-viewing endoscope.
Figure 5:
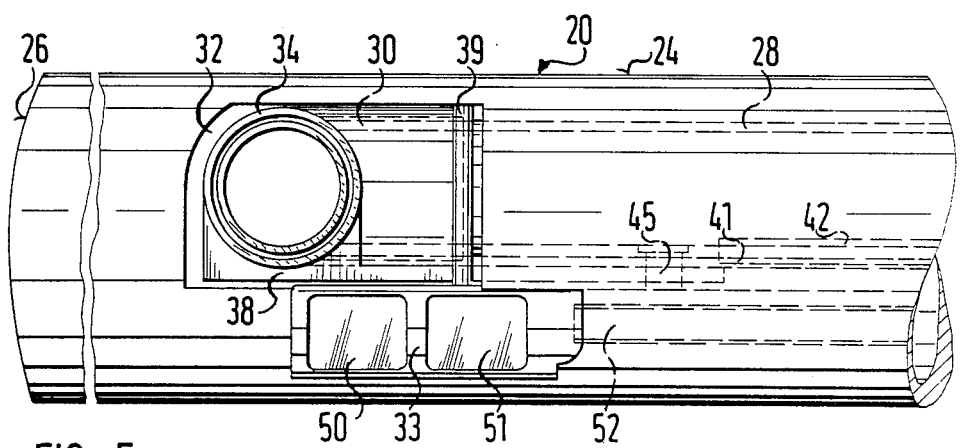
FIG. 5 is a side view of the distal end of the side-viewing endoscope of FIG. 4.

FIGS. 4 and 5 show a practical embodiment of a distal end of a side-viewing endoscope 20. In this region, the sideviewing endoscope 20 is formed by a flexible, hose-like shaft part 24 that forms a floor 26 at its end. An instrumentation channel 28 is arranged relative to the shaft part 24, this instrumentation channel 28 proceeding essentially parallel to the side wall 29 of the shaft part 24 and being arranged in tight proximity thereto. In its lower region, the instrumentation channel 28 comprises a curved section 30. This describes an angle of essentially 90° and leads to a lateral opening 32 in the wall of the shaft part 24. A deflecting element 34 is seated on the curved section 30, this deflecting element 34 comprising a closed pipe section that is held by a pivot bearing element 38. The pivot bearing element 38 is seated on a rotational axis 39 that is arranged tightly proximate to the wall of the shaft part 24 and close to the limitation of the opening 32.

A traction wire mechanism that leads to the head of the endoscope is provided for the actuation of the deflecting element 34. A tube or, respectively, channel 40 is provided parallel to the shaft part 24 for this purpose, traction wires 41, 42 that are conducted to fastening points 43, 44 arranged at the pivot bearing element 38 and are secured there, being guided in this tube or, respectively, channel 40. The traction wires are thereby guided around a deflecting roller 45 that is arranged in the end region of the instrumentation channel 28 and is seated at the shaft part 24. A first traction wire 41 leads to a first fastening point 43 that is provided in order to move the pivot bearing element 38 and, thus, the deflecting element 34 out of its initial position (shown in solid lines in FIG. 4) into an extended position 43' in which the pivot bearing element 38 together with the deflecting element 34 are extended by, for example, 45°, thereby enabling a deflection of 13520. The other traction wire 42 is attached to the fastening point 44. This traction wire serves the purpose of returning the pivot bearing element 38 and the deflecting element 34 back into their initial position. As already recited above with respect to the embodiment of FIGS. 1 and 2, the deflecting element 34 and the curved section 30 of the instrumentation channel are expediently provided with a glide coat or with special rolling bearings in order to assure an easy actuation.

FIG. 5 shows a sideview of the side-viewing endoscope 20. It may be seen from this view that the opening 32 has a roughly rectangular cross-section and that a further opening 33 is provided adjacent to the opening 32, a light source 50 and an objective 51 being arranged in this further opening 33. A water channel 52 that is arranged in the shaft part 24 proceeding parallel to the instrumentation channel also discharges in this opening 33.

I claim:

1. A side viewing endoscope comprising a hollow shaft having a distal end and a lateral wall with an outlet opening adjacent the distal end; an instrumentation channel being disposed in said shaft and having a distal end with a curved section terminating adjacent said outlet opening, said channel having a diameter and a radius of curvature for the curved section matched to each other to guide a complementary instrument out of said outlet opening at an angle to the axis of the shaft in a range of 60°-90°; and a deflection element being mounted adjacent said curved section for transverse movement to the axis of said shaft from a position withdrawn from the outlet opening to a position increasing the curved path of said curved portion by an amount in the range of 60°-90° so that an instrument being guided out of said outlet opening can be deflected up to an additional 90° by said element.

2. A side viewing endoscope according to claim 1, wherein the instrumentation channel is a hollow, tubular member.

3. A side viewing endoscope according to claim 1, wherein the deflecting element is curved in a longitudinal direction, and said element is moved on a curved path having a radius of curvature substantially the same as the curved section of the instrument channel.

4. A side viewing endoscope according to claim 3, wherein the deflection element is curved in a transverse direction.

5. A side viewing endoscope according to claim 4, wherein the deflecting element is the form of a partially closed sleeve.

6. A side viewing endoscope according to claim 5, wherein the deflecting element is mounted for pivotable movement by a pivotable bearing element disposed on the radius of curvature of said curved section.

7. A side viewing endoscope according to claim 6, which includes actuating means for pivoting the deflecting element between the two positions including traction wires with one wire being guided around a deflection shaft to engage the deflection element at a point spaced from the point engaged by the other wire.

8. A side viewing endoscope according to claim 1, which includes means for mounting said deflecting element for sliding movement in said endoscope.

9. A side viewing endoscope according to claim 8, wherein the means for mounting comprises a slide bearing having a glide coat.

10. A side viewing endoscope according to claim 8, wherein the means for mounting includes a roller bearing receiving said deflecting element.

11. A side viewing endoscope comprising a hollow shaft having a closed distal end and a lateral wall with an outlet opening adjacent the distal end; an instrumentation channel comprising a hollow tube being disposed in said shaft and having a distal end with a curved section with a radius of curvature terminating adjacent said outlet opening, said tubular channel having a diameter and a radius of curvature for the curved section matched to each other to guide a complementary instrument out of said outlet opening at an angle to the axis of the shaft in a range of 60°-90°; a deflection element; and means for mounting said deflection element adjacent said curved section for transverse movement along a curved path between a retracted position to an extended position extending through said outlet opening to increase the effective curvature of the curved portion by an amount in the range of 60°-90° so that an instrument being guided out of said outlet opening can be deflected up to an additional 90° by said element.

12. A side viewing endoscope according to claim 11, wherein the means for mounting includes a bearing mounted on the curved section, said bearing allowing sliding movement of the element along said curved path.

13. A side viewing endoscope according to claim 12, wherein the deflecting element has a curvature in the longitudinal direction substantially similar to the curvature of said curved section of said channel.

14. A side viewing endoscope according to claim 11, wherein the deflecting element has a curvature substantially the same as the curvature of said curved section, said deflecting element being mounted by said means for mounting for pivotable movement on an axle positioned adjacent the center of curvature for the curved section.

15. A side viewing endoscope according to claim 14, wherein the deflection element has a curvature in the transverse direction.

* * * * *